(12) United States Patent
Medoro et al.

(10) Patent No.: US 9,950,322 B2
(45) Date of Patent: Apr. 24, 2018

(54) MICROFLUIDIC DEVICE FOR THE MANIPULATION OF PARTICLES

(75) Inventors: Gianni Medoro, Casalecchio di Reno (IT); Nicolò Manaresi, Bologna (IT)

(73) Assignee: Menarini Silicon Biosystems S.p.A., Castel Maggiore (IT)

( * ) Notice: Subject to any disclaimer, the term of this patent is extended or adjusted under 35 U.S.C. 154(b) by 0 days.

(21) Appl. No.: 13/994,158

(22) PCT Filed: Dec. 22, 2011

(86) PCT No.: PCT/IB2011/055920
§ 371 (c)(1),
(2), (4) Date: Aug. 26, 2013

(87) PCT Pub. No.: WO2012/085884
PCT Pub. Date: Jun. 28, 2012

(65) Prior Publication Data
US 2013/0343966 A1 Dec. 26, 2013

(30) Foreign Application Priority Data

Dec. 22, 2010 (IT) .............................. BO2010A0755

(51) Int. Cl.
| | | |
|---|---|---|
| *B01L 3/00* | (2006.01) | |
| *B03C 5/02* | (2006.01) | |
| *G01N 27/447* | (2006.01) | |

(52) U.S. Cl.
CPC ... *B01L 3/502715* (2013.01); *B01L 3/502761* (2013.01); *B03C 5/026* (2013.01);
(Continued)

(58) Field of Classification Search
CPC ........ C12Q 2565/629; B01L 2200/027; G01N 27/44791; B01D 63/088; C12M 23/16;
(Continued)

(56) References Cited

U.S. PATENT DOCUMENTS

| | | |
|---|---|---|
| 5,252,493 A | 10/1993 | Fujiwara et al. |
| 5,279,493 A | 1/1994 | Halder |

(Continued)

FOREIGN PATENT DOCUMENTS

| | | |
|---|---|---|
| DE | 3931851 | 4/1991 |
| DE | 10203636 | 8/2003 |

(Continued)

OTHER PUBLICATIONS

International Preliminary Report on Patentability, International Application No. PCT/IB2011/055920, dated Jun. 25, 2013.
(Continued)

*Primary Examiner* — Lyle Alexander
*Assistant Examiner* — Bryan Kilpatrick
(74) *Attorney, Agent, or Firm* — Marshall, Gerstein & Borun LLP

(57) ABSTRACT

A microfluidic device for isolating particles of at least one given type of a sample; the device is designed to be connected to an apparatus through a plurality of electrical connectors and comprises a system of microfluidic channels and a flash memory, which contains information on the structure (arrangement and geometry of the various components) of the system of microfluidic channels, a map of non-functioning parts of the device, the maximum number of uses and the maximum time of use of the device; the memory has portions allocated for storing the number of times and the time of use of the device.

16 Claims, 1 Drawing Sheet

(52) U.S. Cl.
CPC ... *B01L 3/502784* (2013.01); *B01L 2200/027* (2013.01); *B01L 2200/04* (2013.01); *B01L 2200/0652* (2013.01); *B01L 2200/141* (2013.01); *B01L 2300/023* (2013.01); *B01L 2300/024* (2013.01); *B01L 2300/0645* (2013.01); *B01L 2300/0816* (2013.01); *B01L 2300/0883* (2013.01); *G01N 27/44791* (2013.01)

(58) Field of Classification Search
CPC ............... G01F 1/588; B81B 2201/051; B81B 2201/058
USPC ................................ 422/504, 502; 73/67.71
See application file for complete search history.

(56) References Cited

U.S. PATENT DOCUMENTS

| | | | |
|---|---|---|---|
| 5,384,028 | A | 1/1995 | Ito |
| 5,690,893 | A | 11/1997 | Ozawa et al. |
| 5,888,370 | A | 3/1999 | Becker et al. |
| 5,945,281 | A | 8/1999 | Prabhu |
| 6,149,789 | A | 11/2000 | Benecke et al. |
| 6,203,683 | B1 | 3/2001 | Austin et al. |
| 6,264,815 | B1 | 7/2001 | Pethig et al. |
| 6,294,063 | B1 | 9/2001 | Becker et al. |
| 6,726,820 | B1 | 4/2004 | Frazier |
| 6,824,664 | B1 | 11/2004 | Austin et al. |
| 6,830,729 | B1 | 12/2004 | Holl et al. |
| 6,838,056 | B2 * | 1/2005 | Foster ............... B01L 3/502761 209/3.1 |
| 6,875,329 | B2 | 4/2005 | Washizu et al. |
| 6,888,721 | B1 | 5/2005 | Moghaddam et al. |
| 6,911,132 | B2 | 6/2005 | Pamula et al. |
| 6,977,033 | B2 | 12/2005 | Becker et al. |
| 7,147,763 | B2 | 12/2006 | Elrod et al. |
| 7,250,933 | B2 | 7/2007 | De Boer et al. |
| 7,307,328 | B2 | 12/2007 | Meyer et al. |
| 7,488,406 | B2 | 2/2009 | Hughes et al. |
| 7,641,779 | B2 | 1/2010 | Becker et al. |
| 8,216,513 | B2 | 7/2012 | Becker et al. |
| 8,349,160 | B2 | 1/2013 | Medoro et al. |
| 8,388,823 | B2 | 3/2013 | Manaresi et al. |
| 2002/0031838 | A1 | 3/2002 | Meinhart et al. |
| 2002/0036139 | A1 | 3/2002 | Becker et al. |
| 2002/0042125 | A1 * | 4/2002 | Petersen et al. ........... 435/287.2 |
| 2002/0070114 | A1 | 6/2002 | Miles |
| 2002/0125138 | A1 | 9/2002 | Medoro |
| 2002/0132316 | A1 | 9/2002 | Wang et al. |
| 2003/0044832 | A1 | 3/2003 | Blankenstein |
| 2003/0047456 | A1 | 3/2003 | Medoro |
| 2003/0073110 | A1 | 4/2003 | Aritomi et al. |
| 2003/0159999 | A1 * | 8/2003 | Oakey et al. ................. 210/695 |
| 2004/0011652 | A1 | 1/2004 | Bressler |
| 2004/0055891 | A1 | 3/2004 | Pamula et al. |
| 2004/0058450 | A1 | 3/2004 | Pamula et al. |
| 2004/0063196 | A1 | 4/2004 | Muller et al. |
| 2004/0092024 | A1 | 5/2004 | Reinhardt et al. |
| 2004/0092025 | A1 | 5/2004 | Mordekhay |
| 2004/0191789 | A1 | 9/2004 | Manaresi et al. |
| 2004/0209354 | A1 | 10/2004 | Mathies et al. |
| 2004/0229210 | A1 | 11/2004 | Sabry et al. |
| 2005/0014146 | A1 | 1/2005 | Manaresi et al. |
| 2005/0214736 | A1 | 9/2005 | Childers et al. |
| 2006/0051775 | A1 | 3/2006 | Bianchi |
| 2006/0086309 | A1 | 4/2006 | Manger et al. |
| 2006/0139638 | A1 | 6/2006 | Muller et al. |
| 2006/0177815 | A1 | 8/2006 | Soh et al. |
| 2006/0223178 | A1 | 10/2006 | Barber et al. |
| 2006/0228749 | A1 | 10/2006 | Wang et al. |
| 2007/0026413 | A1 | 2/2007 | Toner et al. |
| 2007/0026415 | A1 | 2/2007 | Fuchs et al. |
| 2007/0051412 | A1 | 3/2007 | Heath et al. |
| 2007/0059683 | A1 | 3/2007 | Barber et al. |
| 2007/0172903 | A1 | 7/2007 | Toner et al. |
| 2007/0250301 | A1 | 10/2007 | Vaisberg et al. |
| 2008/0058991 | A1 | 3/2008 | Lee et al. |
| 2008/0246489 | A1 | 10/2008 | Coster et al. |
| 2008/0264068 | A1 | 10/2008 | Nakasuka et al. |
| 2009/0205963 | A1 | 8/2009 | Medoro et al. |
| 2009/0218223 | A1 | 9/2009 | Manaresi et al. |
| 2010/0035292 | A1 | 2/2010 | Levhenko et al. |
| 2010/0248285 | A1 | 9/2010 | Manaresi |
| 2010/0331205 | A1 | 12/2010 | Medoro |
| 2011/0050200 | A1 | 3/2011 | Tartagni et al. |
| 2011/0193006 | A1 | 8/2011 | Simone et al. |
| 2012/0071335 | A1 | 3/2012 | Manaresi et al. |
| 2012/0091001 | A1 | 4/2012 | Manaresi et al. |
| 2012/0184010 | A1 | 7/2012 | Medoro et al. |
| 2013/0037139 | A1 | 2/2013 | Manaresi et al. |
| 2013/0042936 | A1 | 2/2013 | Calanca et al. |
| 2013/0045144 | A1 | 2/2013 | Perozziello et al. |
| 2013/0118903 | A1 | 5/2013 | Becker et al. |

FOREIGN PATENT DOCUMENTS

| | | |
|---|---|---|
| DE | 10352887 | 4/2005 |
| DE | 19500660 | 12/2007 |
| EP | 1145766 | 10/2001 |
| EP | 1179585 | 2/2002 |
| EP | 1304388 | 4/2003 |
| JP | 58211272 | 12/1983 |
| JP | 2002-536167 A | 10/2002 |
| JP | 2002311461 | 10/2002 |
| JP | 2002536167 | 10/2002 |
| JP | 2003121886 | 4/2003 |
| JP | 2003202604 | 7/2003 |
| JP | 2004000935 | 1/2004 |
| JP | 2005501296 | 1/2005 |
| JP | 2006-524797 A | 11/2006 |
| JP | 2007017163 | 1/2007 |
| JP | 2009-14736 | 1/2009 |
| WO | WO-91/07660 | 5/1991 |
| WO | WO-91/08284 | 6/1991 |
| WO | WO-98/04355 | 2/1998 |
| WO | WO-99/17883 | 4/1999 |
| WO | WO-00/28313 | 5/2000 |
| WO | WO-00/47322 | 8/2000 |
| WO | WO-00/69565 | 11/2000 |
| WO | WO-02/12896 | 2/2002 |
| WO | WO-03/014739 | 2/2003 |
| WO | WO-03/045556 | 6/2003 |
| WO | WO-2004/030820 | 4/2004 |
| WO | WO-2004/071668 | 8/2004 |
| WO | WO-2005/060432 | 7/2005 |
| WO | WO-2005/064325 | 7/2005 |
| WO | WO-2005/098395 | 10/2005 |
| WO | WO-2006/003214 | 1/2006 |
| WO | WO-2006/018849 | 2/2006 |
| WO | WO-2007/010367 | 1/2007 |
| WO | WO-2007/049103 | 5/2007 |
| WO | WO-2007/049120 | 5/2007 |
| WO | WO-2007/110739 | 10/2007 |
| WO | WO-2007/116312 | 10/2007 |
| WO | WO-2007/147018 | 12/2007 |
| WO | WO-2007147076 | 12/2007 |
| WO | WO-2008/11274 | 1/2008 |
| WO | WO-2008/131035 | 10/2008 |
| WO | WO-2009/022222 A2 | 2/2009 |
| WO | WO-2009/137415 A2 | 11/2009 |
| WO | WO-2010/106434 A1 | 9/2010 |

OTHER PUBLICATIONS

International Search Report and Written Opinion, International Application No. PCT/IB2011/055920, dated Mar. 30, 2012.
Altomare et al., Levitation and movement of human tumor cells using a printed circuit board device based on software-controlled dielectrophoresis, Biotechnol. Bioeng., 82(4):474-9 (2003).
Berthier et al., NSTI Nanotech 2005, vol. 1 (2005), www.nsti.org.
Bonci et al., The miR-15a-miR-16-1 cluster controls prostate cancer by targeting multiple oncogenic activities, Nat. Med., 14:1271-7 (2008).

(56) References Cited

OTHER PUBLICATIONS

Cheung et al., Impedance spectroscopy flow cytometry: on-chip label-free cell differentiation, Cytometry Part A, 65A(2):124-32 (2005).
Fiedler et al., Electrocasting formation and structuring of suspended microbodies using A.C. generated field cages, Microsystem Technologies, Berlin, Germany, pp. 1-7 (Dec. 1, 1995).
Fuchs et al., Electronic sorting and recovery of single live cells from microlitre sized samples, Lab Chip, 6:121-6 (2006).
Fuhr et al., Positioning and manipulation of cells and microparticles using miniturized electric field traps and travelling waves, Sensors and Materials, 7(2):131-146 (1995).
Gascoyne et al., Dielectrophoresis-based programmable fluidic processors, Lab Chip, 4:299-304 (2004).
Gascoyne et al., Particle separation by dielectrophoresis, Electrophoresis, 23(13): 1973-83 (2002).
Green et al., Ac Electrokinetics: a survey of sub-micrometre particle dynamics, J. Phys. D: Appl. Phys., 33:632-41 (Dec. 10, 1999).
Hughes, Strategies for dielectrophoretic separation in laboratory-on-a-chip systems, Electrophoresis, 23(16): 2569-82 (2002).
Jones, An electromechanical interpretation of electrowetting, J. Micromech. Microeng., 15(6):1184-7 (2005).
Klein et al., Comparative genomic hybridization, loss of heterozygosity, and DNA sequence analysis of single cells, Proc. Natl. Acad. Sci. USA, 96(8):4494-9 (1999).
Manaresi et al., A CMOS chip for individual cell manipulation and detection, IEEE Journal of Solid-State Circuits, 38 (12):2297-305 (2003).
Medoro et al., A lab-on-a-chip for cell detection and manipulation, IEEE Sensors Journal, 3(3):317-25 (2003).
Medoro et al., A lab-on-a-chip for cell separation based on the moving-cages approach, Proceedings of the 16th Conference on Solid State Transducers, pp. 500-501 (Sep. 15, 2002).
Medoro et al., Dielectrophoretic cage-speed separation of bioparticles, Sensors, Proceedings of the IEEE Vienna, Austria, Oct. 24-27, 2004, pp. 76-79.
Milner et al., Dielectrophoretic classification of bacteria using differential impedance measurements, Electronics Letters, 34(1):66-8 (1998).
Nagrath et al., Isolation of rare circulating tumour cells in cancer patients by microchip technology, Nature, 450(7173):1235-9 (2007).
Nieuwenhuis et al., Near-field optical sensors for particle shape measurements, Sensors Journal IEEE, 3(5):646-51 (2003).
O'Hara et al., Ratcheting electrophoresis microchip (REM) for programmable transport and separation of macromolecules, Proceedings of the International Mechanical Engineering Congress and Exposition, 3:619-28 (2001).
Ohta et al., Tech. Dig. of the Solid State Sensor, Actuator and Microsystems, Workshop, pp. 216-219 (2004).
Petersson et al., Carrier medium exchange through ultrasonic particle switching in microfluidic channels, Anal. Chem., 77:1216-21 (2005).
Pethig et al., Enhancing traveling-wave dielectrophoresis with signal superposition, IEEE Eng. Med. Biol. Mag., 22(6):43-50 (2003).
Reichle et al., Combined laser tweezers and dielectric field cage for the analysis of receptor-ligand interactions on single cells, Electrophoresis, 22(2):272-82 (2001).
Romani et al., Capacitive sensor array for localization of bioparticles in CMOS lab-on-a-chip, Proc. Int. Solid State Circuit Conference, 1:224-5 (2004).
Rousselet et al., Directional motion of brownian particles induced by a periodic asymmetric potential, Nature, 370(6489):446-8 (1994).
Schnelle et al., Three-dimensional electric field traps for manipulation of cells—calculation and experimental verfication, Biochem. Biophys. Acta, 1157(2):127-40 (1993).
Stoecklein et al., Direct genetic analysis of single disseminated cancer cells for prediction of outcome and therapy selection in esophageal cancer, Cancer Cell, 13:441-53 (2008).
Suehiro, The dielectrophoretic movement and positioning of a biological cell using a three-dimensional grid electrode system, J. Phys. D: Appl. Phys., 31:3298-305 (1998).
Zieglschmid et al., Detection of disseminated tumor cells in peripheral blood, Crit. Rev. Clin. Lab. Sci., 42(2):155-96 (2005).
Office Action (Japanese), Japanese Patent Application No. 2013/545619, dated Jul. 31, 2015.

\* cited by examiner

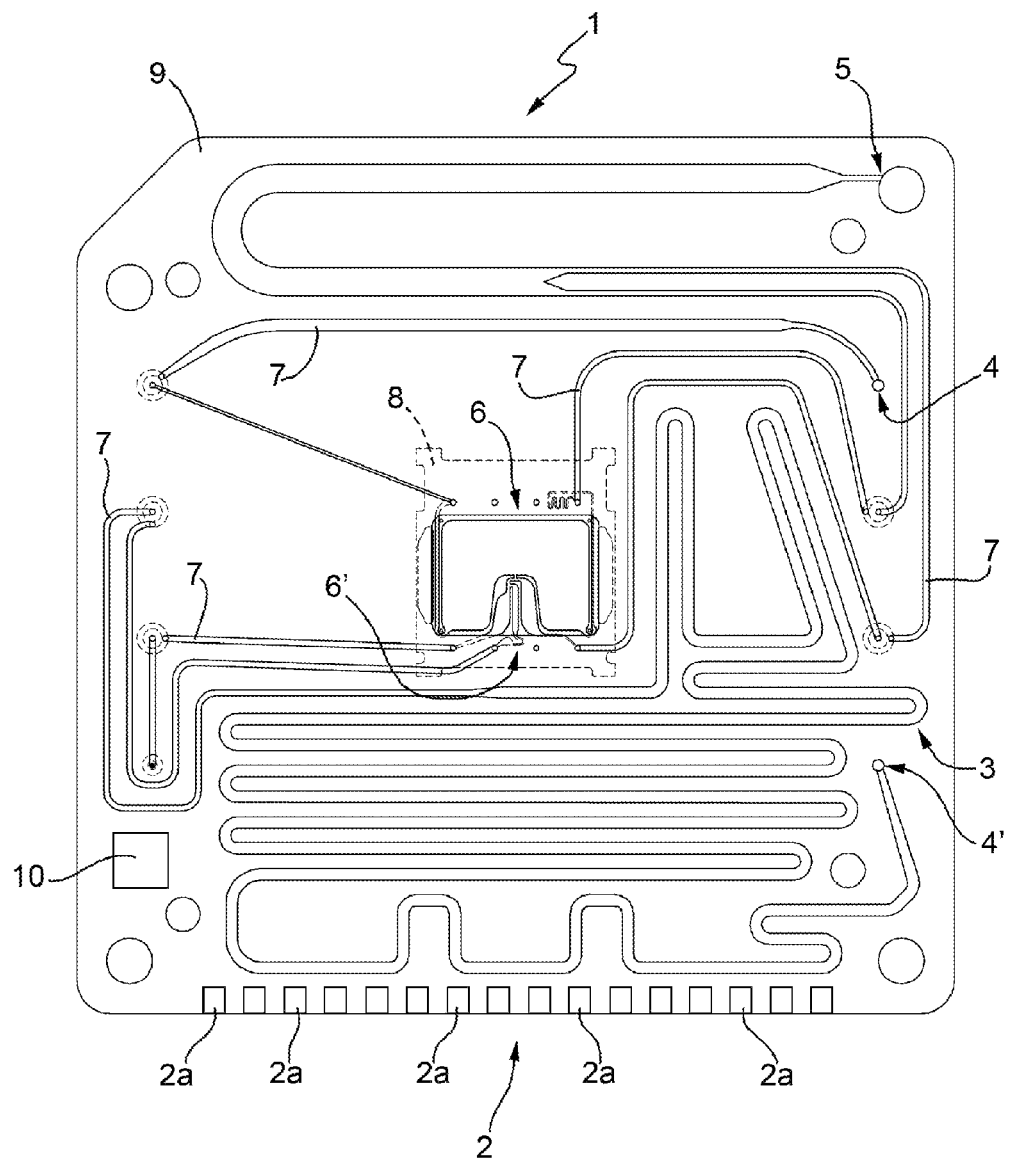

MICROFLUIDIC DEVICE FOR THE MANIPULATION OF PARTICLES

CROSS-REFERENCE TO RELATED APPLICATIONS

This is the U.S. national phase of International Application No. PCT/IB2011/055920, filed Dec. 22, 2011, which claims the benefit of Italian patent Application No. BO2010A000755, filed Dec. 22, 2011.

TECHNICAL FIELD

The present invention relates to a microfluidic device and to uses of such a device.

BACKGROUND OF THE INVENTION

The patent application PCT/IB2010/000615 discloses a microfluidic device for manipulating particles of a sample (in particular, for isolating a given type of particles from other particles). Such a device has relatively small dimensions and can be thrown away after use so as not to contaminate a possible further sample to be manipulated subsequently. Said device is typically used in combination with a fixed apparatus of larger dimensions, which comprises an electronic control unit and governs the various components of the device. The device is provided with a separation chamber, within which, in use, manipulation of particles takes place according to what is described in one or more of the patent applications with publication numbers WO0069565, WO2007010367, WO2007049120, and WO2007116312.

One and the same apparatus may be able to use different devices for different uses.

Since the devices described above are frequently used in the diagnostic field, it is very important for them to be managed with the maximum precision and care. Currently, no system is envisaged to prevent human-error in management of the devices and/or for driving different components of the devices so as to optimize operation even in the case of defects of the devices themselves that are relatively small (and hence negligible for normal operation thereof).

The U.S. Pat. No. 6,726,820 describes a microdevice equipped with an integrated readable, writable, and rewritable memory.

The patent document No. DE10352887 describes a DNA-Chip-Array-Processor equipped with a memory containing some information.

The U.S. Pat. No. 5,690,893 describes an analyser equipped with a non-volatile memory containing a condition of analysis.

The patent document No. US2004092024 describes a plurality of supporting plates for samples with a resettable memory.

The U.S. Pat. No. 5,384,028 describes a biosensor equipped with a memory for storing data that include data regarding fabrication of the biosensor.

The patent document No. WO2005064325 describes a reusable cartridge for bio-analyses including a rewritable non-volatile memory.

The patent document No. WO2009137415 relates to droplet actuators.

The patent document No. WO0047322 describes an apparatus for moving elements (packets) along given paths. It does not describe memory media on devices of the disposable type.

None of the U.S. Pat. No. 6,726,820, DE10352887, U.S. Pat. No. 5,690,893, US2004092024, U.S. Pat. No. 5,384,028, WO2005064325, WO2009137415, and WO0047322 envisages a system for driving different components of the devices so as to optimize operation also in the case of defects of the devices themselves that are relatively small (and hence negligible for normal operation thereof).

The aim of the present invention is to provide a device and uses of said device that will enable the limits of the prior art to be overcome, at least partially, and that will, at the same time, be easy and economically advantageous to produce.

SUMMARY

According to the present invention, a device and uses of said device are provided according to what is claimed in the ensuing independent claims and, preferably, in any one of the claims that depend directly or indirectly upon the independent claims.

Unless otherwise explicitly specified, in the present text the terms listed below have the meaning indicated hereinafter.

By "equivalent diameter of a section" is meant the diameter of a circle having the same area as the cross section.

By "section" of a channel or a duct is meant the cross section of the lumen of the channel substantially perpendicular to the longitudinal extension of the channel (or duct), i.e., to the direction of advance of the fluid in the channel (or duct).

By "microfluidic system (or device)" is meant a system (or device) comprising at least one microfluidic channel (or duct) and/or a microfluidic chamber.

By "microfluidic chamber" is meant a chamber delimiting an internal space having one of its own dimensions (in particular, the height) of less than 1 mm.

By "microfluidic channel (or duct)" is meant a channel (or duct) having a cross section with equivalent diameter of less than 1 mm.

The dimensions of the channels or ducts or chambers can be measured in a standard way with profilometers.

In the present text, by "particle" is meant a corpuscle having the largest dimension of less than 500 µm (advantageously, less than 150 µm). Non-limiting examples of particles are: cells, cellular detritus (in particular, cellular fragments), cellular aggregates (such as, for example, small clusters of cells deriving from stem cells such as neurospheres or mammospheres), bacteria, liposheres, (polystyrene and/or magnetic) microspheres, nanospheres (for example, nanospheres of up to 100 nm), complexes formed by microspheres bound to cells, etc. Advantageously, the particles are cells.

According to some embodiments, the particles (advantageously cells and/or cellular detritus) have the largest dimension of less than 60 µm.

The dimensions of the be measured in a standard way with microscopes with graduated scale or normal microscopes used with slides (deposited on which are the particles) with graduated scale.

In the present text, by "dimensions of a particle" is meant the length, width, and thickness of the particle.

The term "substantially selective" is used for identifying a displacement (or other similar terms indicating a movement and/or a separation) of particles, where the particles that are displaced and/or separated are particles that for the most part are constituted by one or more given types. Advantageously, a substantially selective displacement (or other similar terms indicating a movement and/or a separation) envisages displacing particles with at least 90% (advantageously 95%) of particles of the given type or types (percentage given by the number of particles of the given type/types with respect to the total number of particles).

BRIEF DESCRIPTION OF THE DRAWING

The invention is described hereinafter with reference to the annexed plate of drawings, which illustrates a non-limiting example of embodiment thereof, and in which:

FIG. 1 is a schematic illustration of a system built in accordance with the present invention

EMBODIMENTS OF THE INVENTION

In accordance with a first aspect of the present invention, a microfluidic device is provided for manipulating at least one given type of particles of a sample. In particular, the device is designed to isolate the aforementioned particles with respect to further particles in a substantially selective way. More in particular, the device is of the disposable type.

In FIG. 1, designated as a whole by 1 is one such device.

The device 1 is designed to be connected to an apparatus (not illustrated) and comprises a connection unit 2 for connecting the device 1 itself to the apparatus electrically (or electromagnetically).

The apparatus is designed to drive different components of the device 1. The apparatus is external to (separate from) the device 1 and can come into contact therewith via the connection unit 2. According to some embodiments, the apparatus has a seat (not illustrated), in which, in use, the device 1 is inserted so as to connect the apparatus to the device 1.

According to the depicted embodiment, the connection unit 2 comprises a plurality of electrical connectors 2a (of which only some are schematically illustrated in FIG. 1), each of which is designed to couple with corresponding connectors (not illustrated) of the apparatus. Advantageously, the connectors 2a are at least partially exposed towards the outside of the device 1. In use, through the connectors 2a the device 1 receives operating commands from the apparatus.

According to further not shown embodiments, the connection unit 2 is able to communicate (receive and/or transmit information and/or commands) in wireless mode (in particular, with the apparatus). This can be particularly useful when it is desired to identify one or more given devices in a group of devices.

By means of the wireless communication it is possible to prevent direct contact between the device 1 and the apparatus. This presents a dual advantage: (i) in the case where the device 1 has been used (biological waste) it prevents contamination of the apparatus; (ii) in the case the device 1 is new, it prevents contamination of the device 1 itself (possibly-sterile or DNA/RNA-free).

The device 1 comprises a microfluidic system 3, which in turn has at least one inlet 4, at least one outlet 5, and at least one (microfluidic) chamber 6, within which, in use, the particles of the given type are manipulated. In particular, the system 3 also comprises at least one microfluidic channel 7. More in particular, the system 3 comprises a plurality of microfluidic channels 7.

According to the embodiment depicted in FIG. 1, the system 3 comprises two inlets 4 and 4', two outlets 5 and 5', and two (microfluidic) chambers 6 and 6'. In the specific case, the chamber 6' comprises three portions of a different shape connected to one another.

The chamber 6 is designed to move the particles of the given type selectively with respect to the further particles of the sample. In particular, in use, the sample is brought into the chamber 6, and the particles of the given type are selectively brought into the chamber 6' previously filled with a liquid transport medium. The particles of the given type are then recovered by an operator through the outlet 5'.

The device 1 comprises a substructure 8, set in a position corresponding to which is the chamber 6 (and the chamber 6'). More in particular, the substructure 8 delimits at the bottom the chamber 6 (and the chamber 6'). The substructure 8 is mainly (more in particular, completely) made of silicon.

The device 1 comprises a plurality of actuators (for example, valves and/or electrodes), which are operated on the basis of commands coming from the apparatus. According to some embodiments, the chamber 6 comprises a plurality of actuators (for moving the particles). The actuators of the device 1 comprise the actuators of the chamber 6 (and/or 6'). The actuators of the chamber 6 (and/or 6') comprise (are), in particular, electrodes.

Driving of the various actuators (electrodes) of the chamber 6 enables displacement of the particles (and is governed by the apparatus). Advantageously, the structure and operation of the chamber 6 (and of the chamber 6') is in accordance with what is described in, one or more of the patent applications with publication numbers WO0069565, WO2007010367, WO2007049120 and WO2007116312 filed in the name of the present applicant.

More in particular, the device 1 presents the same structure and operation as the device described in the patent application PCT/IB2010/000615 (publication No. WO2010106434) filed in the name of the present applicant. The device 1 differs from the one described in the patent application PCT/IB2010/000615 owing to the presence of a partially rewritable memory as described hereinafter. Likewise, the apparatus presents the same structure and operation as the apparatus described in the patent application PCT/IB2010/000615.

According to the depicted embodiment, the device 1 also comprises an element 9 (in particular, made of plastic material), made in which are the inlet 4 (and 4') and the outlet 5 (and 5'). Also made in the element 9 are the microfluidic channels 7 and (partially) the chamber 6 (and 6'). More in particular, the system 3 is at least partially (according to some embodiments, completely) made in the element 9.

Advantageously, the element 9 comprises (more specifically, mainly, consists of) plastic material.

According to specific embodiments, the device 1 comprises a printed circuit board (PCB—not shown). The PCB is connected to the connection unit 2 and to the substructure 8. The PCB is set underneath the element 9.

The device 1 further comprises a non-volatile rewritable memory (a flash memory). More in particular, the device 1 comprises a physical medium 10 for said memory.

According to some embodiments (as the one depicted), the physical medium 10 of the memory is set in the area of the element 9 separately (i.e., in a different position) from the substructure 8. In this way, it is possible to reduce the manufacturing costs.

According to further embodiments (not illustrated), the physical medium 10 of the memory is set in a position corresponding to the substructure 8. The physical medium 10 is connected to the PCB.

In particular, the memory contains information on the device 1.

Advantageously, the memory contains information on the type of device 1. Advantageously, the information on the type of device 1 is stored at least partially (in particular, completely) in a non-rewritable (read-only) area of the memory.

In particular, the information on the type of device 1 comprises information on the structure (arrangement and geometry of the various components) of the device 1. More in particular, the information on the type of device 1 comprises information on the structure (arrangement and geometry of the various components), of the microfluidic system 3. In this way, the apparatus (more in particular, the control unit of the apparatus) is able to recognize the device 1 and drive its own actuators (and hence the various components of the device 1 itself) in an appropriate way. The information on the structure of the device 1 (in particular, of the microfluidic system 3) is written in the memory at the time of testing of the device 1 and is of the read-only type (i.e., it cannot be modified).

According to some embodiments, the information on the type of device 1 comprises information on the structure (arrangement and geometry of the various components) of the PCB. In this way, the apparatus (more in particular, the control unit of the apparatus) is able to recognize the device 1 and drive the PCB in an appropriate way. The information on the structure of the PCB is written in the memory at the time of testing of the device 1 and is of the read-only type (i.e., it cannot be modified).

Advantageously, the information on the type of device 1 comprises an indication of the actuators (in particular, electrodes) of the device 1 that are faulty. In particular, the indication of the faulty actuators comprises (more in particular, is) the indication of the faulty actuators (in particular, electrodes) of the chamber 6 (and/or 6').

More precisely, the information on the type of device 1 comprises the position/positions of the faulty electrode/electrodes. In other words, the memory comprises a mapping of the faulty electrodes. This information is written in the memory at the time of testing of the device 1. This information is of the read-only type (i.e., it cannot be modified). Typically, the faulty electrodes are non-functioning or in any case unable to guarantee proper operation.

With this type of information, the apparatus (in particular, the control unit of the apparatus) manipulates (more precisely, moves) the particles (in particular, the particles of the given type) so as to prevent area/areas where the faulty electrode/electrodes is/are set. In other words, the electrodes are actuated so as to impose on the particles one or more paths that do not pass in a position corresponding to the faulty electrode/electrodes.

In this way, the very important advantage is achieved of rendering possible use of the device 1 even when it has small defects.

This enables significant reduction in the number of rejects of the devices 1 at the end of production, when the devices 1 are tested, without reducing the quality of the results in use of the devices 1 themselves. It is thus possible to reduce considerably the manufacturing costs.

According to some embodiments, the information on the type of device 1 comprises the maximum number of uses that can be performed. This information is written in the memory at the time of testing of the device 1. This information is of the read-only type (i.e., it cannot be modified).

Advantageously, the memory is designed to store the number of times that the device 1 is used. In particular, a portion of the memory is allocated for storage of the number of times that the device 1 is used.

In use, whenever the device 1 is used, the apparatus (in particular, the control unit of the apparatus) records said use in the memory. When the apparatus (in particular, the control unit of the apparatus) detects (by reading the memory) that the maximum number of uses has been reached, the apparatus itself blocks operation and issues a corresponding error signal.

In this way, it is possible to guarantee a high quality level in use of the device 1. In particular, for example, in its use for diagnostic purposes, the device 1 can be used just once to prevent contamination of the samples. In this case, what is described enables prevention of errors by the operator and, hence, potential incorrect results.

According to some embodiments, the information on the type of device 1 contains the maximum time of use of the device 1. This information is written in the memory at the time of testing of the device 1. This information is of the read-only type (i.e., it cannot be modified).

Advantageously, the memory is designed to store the time during which the device 1 is used. In particular, a portion of the memory is allocated for storage of the time during which the device 1 is used.

In use, whenever the device 1 is used, the apparatus (in particular, the control unit of the apparatus) records the time of said use in the memory and possibly adds it to the time already present in the memory itself. When the apparatus (in particular, the control unit of the apparatus) detects (by reading the memory) that the maximum time of use has been reached, the apparatus itself blocks operation and issues a corresponding error signal.

In this way, it is possible to guarantee a high quality level in use of the device 1. In particular, it is thus possible to prevent a device 1 that is worn out (owing to excessive use) from being used again.

Advantageously, the memory is accessible via password. In this way, it is possible to reduce the risks of said memory being tampered with.

Advantageously, the memory is encrypted. In this way, the possibility of the device 1 being used in combination with unsuitable apparatuses is prevented.

Advantageously, the information on the type of device 1 comprises the expiry date of the device 1. This information is written in the memory at the time of testing of the device 1. This information is of the read-only type (i.e., it cannot be modified). In use, when the apparatus (in particular, the control unit of the apparatus) detects (by reading the memory) that the expiry date is passed, the apparatus itself blocks operation and issues a corresponding error signal.

Also in this way the quality and safety of operation is improved.

According to some embodiments, the information on the type of device 1 comprises the position of the microfluidic system 3 (in the case where the latter has been produced by means of lithographic techniques) with respect to the substructure (wafer) 8. The memory further comprises the identifier of the substructure (wafer) 8 within each production lot and the identifier of the lot itself. This information is written in the memory at the time of testing of the device 1. This information is of the read-only type (i.e., it cannot be modified).

According to some embodiments, the information on the type of device 1 comprises an indication on whether the information on the faulty actuators (electrodes) is present or not (for example: 1=yes, 0=no). This indication is written in the memory at the time of testing of the device 1 and is of the read-only type (i.e., it cannot be modified).

According to some embodiments, the information on the type of device 1 comprises an indication on the type of error (for example, a code and/or a coloured marker). Advantageously, the information on the type of device 1 moreover contains an indication of the model of the device 1 (each revision or new version of the device 1 can require different operating procedures that can possibly also be stored in the memory). According to some particular embodiments, the information on the type of device 1 contains an indication on the type of mask (or masks) that has (have) been used for producing the element 9.

According to some embodiments, the information on the type of device 1 comprises information on the bonding system that has been used for producing the device 1. This information is written in the memory at the time of testing of the device 1. This information is of the read-only type (i.e., it cannot be modified).

According to some embodiments, the information on the type of device 1 comprises information on the height of the chamber 6 (and/or 6') (for example, 90 μm). This information is written in the memory at the time of testing of the device 1. This information is of the read-only type (i.e., it cannot be modified).

According to some embodiments, the information on the type of device 1 comprises information on the maximum number of droplets that can be recovered per sample (in particular through the outlet 5'). Said droplets are the ones that contain (or in any case should contain) the particles of the given type. This information is written in the memory at the time of testing of the device 1. This information is of the read-only type (i.e., it cannot be modified).

According to some embodiments, the information on the type of device 1 comprises information on the average volume of the aforementioned droplets. This information is written in the memory at the time of testing of the device 1. This information is of the read-only type (i.e., it cannot be modified).

According to some embodiments, the information on the type of device 1 comprises information on the authorisation of the device 1 for use of different transport solutions (for example PBS—phosphate buffered saline solution). This information is written in the memory at the time of testing of the device 1. This information is of the read-only type (i.e., it cannot be modified).

In use, the transport solution is brought into the chamber 6' prior to selective displacement of the particles of the given type.

According to some embodiments, the information on the type of device 1 comprises information on the range of operating temperatures (for example, 277K-309K). This information is written in the memory at the time of testing of the device 1. This information is of the read-only type (i.e., it cannot be modified).

According to some embodiments, the memory is designed to contain (in particular, has a portion allocated for storing) information on whether the device 1 has been inserted in the apparatus but not expelled (for example: 1=yes, 0=no). This information is written in the memory at the time of use of the device 1 (by the apparatus—more in particular, by the control unit of the apparatus). According to some embodiments, upon charging (in particular, immediately after charging), the information on charging is written (for example by writing 1). Upon expulsion (in particular, immediately prior to expulsion), the information on the expulsion is written (for example, by writing 0).

This information indicates when the device 1 has been charged into the apparatus but has never been expelled therefrom and has the purpose of enabling prosecution of the experiment in the case of reboot of the apparatus subsequent to charging. When the device 1 is removed with the apparatus turned off manually by a technician, the device 1 should no longer be used, and it is advantageous for the apparatus to be able to detect when the memory has this variable equal to 0 and consequently understands that the device 1 has been moved away and may have been tampered with, thus preventing continuation of the experiment.

According to some embodiments, the memory is designed to contain (in particular, has a portion allocated for storing) one or more of the following items of information: date and time of start of experiment (writing in the memory is performed at start of the experiment); date and time of insertion of the device 1 into the apparatus 1 (writing in the memory is performed immediately after insertion); date and time of the end of the experiment (writing in the memory is performed at the end of the experiment); date and time of expulsion of the device 1 from the apparatus (writing in the memory is performed just before expulsion); set of parameters used (in particular, transport solutions used—for example, PBS) (writing in the memory is performed at start of the experiment); an identifier of the apparatus used (writing in the memory is performed immediately after insertion); name of the pattern used (i.e., the configuration of the electrophoresis; field, i.e., the association between each electrode and each phase—Vp or else Vm (the energizing potentials that can be assumed by the electrodes)) (writing in the memory is performed at start of the experiment); frequency, amplitude and phase delta for Vp, Vm and Vlid (the potential for energizing the lid) (writing in the memory is performed at start of the experiment).

According to some embodiments, the information on the type of device 1 comprises a combination of a number of the types of information referred to above.

Advantageously, the memory contains information on how the device 1 must be made to work (namely, information on which operating procedures must be implemented, for example, how the various actuators are to be actuated).

According to some variants, the information contains indications of the use (for example, for research use only or else for in vitro diagnostics).

According to some embodiments, the memory contains information chosen from among: information on the type of device 1, information on how the device 1 is to be made to work, and a combination thereof.

Advantageously, the information on how the device 1 is to be made to work is stored at least partially (in particular, completely) in a non-rewritable (read-only) area of the memory.

According to some embodiments, the memory comprises at least one identifier of the device 1 (namely, a unique identifier code of the device 1). In other words, the memory of each device 1 contains an identifier different from the identifier of the other devices. This information is written in the memory at the time of testing of the device 1.

Advantageously, the identifier of the device 1 is stored at least partially (in particular, completely) in a non-rewritable (read-only) area of the memory.

According to some embodiments, the memory contains information chosen from among: information on the type of device 1, information on how the device 1 is to be made to work, at least one identifier of the device 1, and a combination thereof.

Advantageously, one or more of the items of information present in the memory can be displayed by means of a human-machine interface (HMI—for example a screen) of the apparatus.

According to a second aspect of the present invention, use of the device 1 for diagnostic purposes is provided.

According to a third aspect of the present invention, use of the device 1 for separating the particles of the given type from other particles is provided.

Unless otherwise explicitly indicated, the contents of the references (articles, books, patent applications, etc.) cited in this text are integrally recalled herein. In particular, the aforementioned references are herein incorporated by reference.

The invention claimed is:

1. A microfluidic device for manipulating particles of at least one given type of a sample, the device (1) being designed to be connected to an apparatus; the device comprising:
 a connection unit (2) for connecting the device (1) itself to the apparatus, which is external to the device (1);
 a microfluidic system (3), comprising:
  at least one inlet (4; 4'),
  at least one outlet (5; 5'),
  at least one microfluidic chamber (6; 6') comprising a plurality of actuators within the chamber for selectively manipulating within the chamber the particles of the at least one given type with respect to other particles of the sample, and
 a non-volatile rewritable memory disposed on the microfluidic device, wherein the memory contains information on the device, which information on the device comprises a map of positions of faulty actuators, and wherein the memory is adapted to be read by a control unit of the apparatus such that the control unit is configured to control the plurality of actuators of the device (1) to actuate so that the particles are moved in a path that does not pass a position corresponding to the positions of the faulty actuators.

2. The device according to claim 1, wherein the information on the device (1) is at least partially set in a non-rewritable area of the memory.

3. The device according to claim 1, wherein the actuators are electrodes; and the identification of faulty actuators comprises an identification of the faulty electrodes.

4. The device according to claim 1, wherein the information on the device (1) further comprises information on the structure (arrangement and geometry of the different components) of the microfluidic system (3).

5. The device according to claim 1, wherein the information on the device (1) further comprises the maximum number of uses that can be performed.

6. The device according to claim 1, wherein the memory is designed to store the number of times that the device (1) is used; in particular, a portion of the memory is allocated for storage of the number of times that the device (1) is used.

7. The device according to claim 1, wherein the information on the device (1) further comprises the maximum time of use of the device (1).

8. The device according to claim 1, wherein the memory is designed to store the time during which the device (1) is used; in particular, a portion of the memory is allocated for storage of the time during which the device (1) is used.

9. The device according to claim 1, wherein the connection unit (2) comprises electrical connectors (2*a*) at least partially exposed towards the outside of the device (1).

10. The device according to claim 1, wherein the memory is accessible by means of a password.

11. The device according to claim 1, wherein the memory is encrypted.

12. The device according to claim 1, and comprising: a silicon substructure (8), in the area of which the chamber (6; 6') is located; an element (9) mainly made of plastic material, in which said inlet (4; 4'), said outlet (5; 5'), and at least one channel (7) of the microfluidic system (3) are obtained; and a physical medium (10) for said memory, said physical medium (10) being set in an area corresponding to the element (9) mainly made of plastic material in a position different from the silicon substructure (8).

13. A system, comprising:
 an apparatus comprising a control unit; and
 a microfluidic device comprising:
  a connection unit for connecting the device to the apparatus,
  a microfluidic system comprising:
   at least one inlet,
   at least one outlet,
   at least one microfluidic chamber comprising a plurality of actuators for selectively moving particles of the given type within the at least one microfluidic chamber, and
  a non-volatile rewritable memory disposed on the microfluidic device and containing information on the device, which information on the device comprises an identification of faulty actuators of the plurality of actuators and their respective locations;
 wherein:
  said microfluidic chamber is designed to move selectively the particles of the at least one given type with respect to other particles of the sample,
  the apparatus is external to the microfluidic device,
  the control unit of the apparatus controls the actuation of the plurality of actuators,
  the control unit is configured to read the memory of the microfluidic device and control the actuation of the plurality of actuators so that the particles are moved in a path that does not pass a position where the faulty actuators are located.

14. The device of claim 1, wherein the mapping of faulty actuators is read-only information written on the memory during testing of the microfluidic device prior to first use of the device.

15. The system of claim 13, wherein the identification of faulty actuators and their respective locations is read-only information written on the memory during testing of the microfluidic device prior to first use of the device.

16. The system of claim 13, wherein the actuators are electrodes.

* * * * *